(12) United States Patent
Hafey et al.

(10) Patent No.: US 7,058,901 B1
(45) Date of Patent: Jun. 6, 2006

(54) METHODS AND APPARATUS FOR CONTROLLING THE DISPLAY OF MEDICAL IMAGES

(75) Inventors: Christopher Hafey, Brisbane, CA (US); Ton van den Hoven, Bilthaven (NL); Tongzhe Cui, San Jose, CA (US); David Lionetti, Pittsburg, PA (US); Paul Joseph Chang, Alison Park, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/696,733

(22) Filed: Oct. 29, 2003

Related U.S. Application Data

(60) Provisional application No. 60/422,040, filed on Oct. 29, 2002.

(51) Int. Cl.
*G06F 17/00* (2006.01)
*G09G 5/00* (2006.01)

(52) U.S. Cl. ................ 715/792; 715/838; 345/619
(58) Field of Classification Search ............ 345/619, 345/629, 650, 661, 660, 157, 1.1, 1.2, 1.3; 715/792, 838
See application file for complete search history.

(56) References Cited

U.S. PATENT DOCUMENTS

| | | | | |
|---|---|---|---|---|
| 5,046,027 A | * | 9/1991 | Taaffe et al. | 345/557 |
| 5,047,754 A | * | 9/1991 | Akatsuka et al. | 345/163 |
| 5,179,651 A | * | 1/1993 | Taaffe et al. | 345/555 |
| 5,404,316 A | * | 4/1995 | Klingler et al. | 715/723 |
| 5,431,161 A | | 7/1995 | Ryals et al. | |
| 5,452,416 A | * | 9/1995 | Hilton et al. | 715/783 |
| 5,537,127 A | * | 7/1996 | Jingu | 345/1.3 |
| 5,542,003 A | | 7/1996 | Wofford | |
| 5,680,152 A | | 10/1997 | Bricklin | |
| 5,954,650 A | | 9/1999 | Saito et al. | |
| 5,986,662 A | | 11/1999 | Argiro et al. | |
| 5,987,345 A | * | 11/1999 | Engelmann et al. | 600/407 |
| 6,128,002 A | * | 10/2000 | Leiper | 345/156 |
| 6,154,601 A | * | 11/2000 | Yaegashi et al. | 386/52 |
| 6,177,937 B1 | | 1/2001 | Stockham et al. | |
| 6,243,095 B1 | * | 6/2001 | Shile et al. | 715/854 |
| 6,269,379 B1 | | 7/2001 | Hiyama et al. | |
| 6,327,420 B1 | * | 12/2001 | Furukawa | 386/52 |
| 2002/0039084 A1 | * | 4/2002 | Yamaguchi | 345/1.1 |
| 2003/0071829 A1 | * | 4/2003 | Bodicker et al. | 345/619 |

FOREIGN PATENT DOCUMENTS

JP        10225441        8/1998
JP        11290279        10/1999

* cited by examiner

*Primary Examiner*—Ryan Yang

(57) ABSTRACT

A navigation rectangle controls display of medical images in a multi-display system. Multiple thumbnail sized medical images are displayed on a control panel. Each navigation rectangle encompasses one or more thumbnail size medical images on the control panel. In turn, images, corresponding to the thumbnail size medical images encompassed by the navigation rectangle, are displayed on a monitor that corresponds to the navigation rectangle. The user may fully move the navigation rectangle to select any images within an exam, and the user may resize the navigation rectangle to include or exclude images. The user may move images in and out of the navigation rectangle.

30 Claims, 5 Drawing Sheets

METHODS AND APPARATUS FOR CONTROLLING THE DISPLAY OF MEDICAL IMAGES

CROSS-REFERENCES TO RELATED APPLICATIONS

This application claims the benefit of U.S. Provisional Patent Application No. 60/422,040, filed Oct. 29, 2002, entitled "Methods and Apparatus For Controlling The Display Of Medical Images."

BACKGROUND OF THE INVENTION

1. Field of the Invention

The present invention is directed toward the field of medical informatics, and more particularly toward a medical informatics system with multiple displays.

2. Art Background

Radiology equipment (e.g., CT scanners, MRI scanners, X-Ray etc.) is in wide spread use as diagnostic tools in hospitals today. Typically, when collecting information from a diagnostic tool, several medical images are generated for subsequent analysis and diagnosis of the patient's medical condition. A collection of medical images that focus on a particular area may be referred to as a "medical exam", and a collection of medical images or medical exams may be referred to as a "study." For example, a study from an X-Ray machine may consist of a number of X-Rays taken from different perspectives of the target area. It is the totality of the study that the physician uses to make a diagnosis of the patient.

It has become more common in the medical field for images to be stored, distributed, and viewed in digital form using computer technology. Currently, Picture Archival and Communication Systems or PACS have been in widespread use. In a typical PACS application, image data obtained by imaging equipment such as CT scanners or MRI scanners are stored in the form of computer data files. The size of a data file for an image varies depending on the size and resolution of the image. For example, a typical image file for a diagnostic-quality chest X-ray is on the order of 10 megabytes (MB). The image data files are usually formatted in a "standard" or widely accepted format. In the medical field, one widely used image format is known as DICOM. The DICOM image data files are distributed over computer networks to specialized viewing stations capable of converting the image data to high-resolution images on a CRT display.

Radiology departments of hospitals often use computer workstations with multiple high-resolution monitors to perform diagnostic analysis on images. As such, it is desirable to develop a user interface for a medical informatics system that allows a user to readily control the display of images on a multiple display system.

SUMMARY OF THE INVENTION

A navigation rectangle permits a user to easily control display of medical images in a multi-display system. Multiple thumbnail sized medical images are displayed on a control panel. In one embodiment, thumbnail size medical images, associated with a medical exam, are displayed horizontally across the control panel. Multiple monitors or displays are used to view the medical images. Each navigation rectangle encompasses one or more thumbnail size medical images on the control panel. In turn, images, corresponding to the thumbnail size medical images encompassed by the navigation rectangle, are displayed on a monitor that corresponds to the navigation rectangle. For example, a first navigation rectangle may encompass images from a first medical exam, and a second navigation rectangle may encompass images from a second medical exam. For this example, the images from the first medical exam are displayed on a first display, and the images from the second medical exam are displayed on a second display. In one embodiment, the user may fully move the navigation rectangle to select any images within an exam, and the user may resize the navigation rectangle to include or exclude images. The user may move images in and out of the navigation rectangle.

DETAILED DESCRIPTION

A medical informatics system provides a means to view medical images and information. In one embodiment, the medical informatics system is used for diagnostic purposes by a radiologist to view medical images. The medical informatics system includes, in part, software for operation on a computer workstation. The computer workstations may have one or more monitors. If the medical informatics system is used to diagnose medical images, the computer workstation includes high-quality monitors suitable for viewing high-resolution images. In one embodiment, the monitors display the images and information in color.

Figure 1:
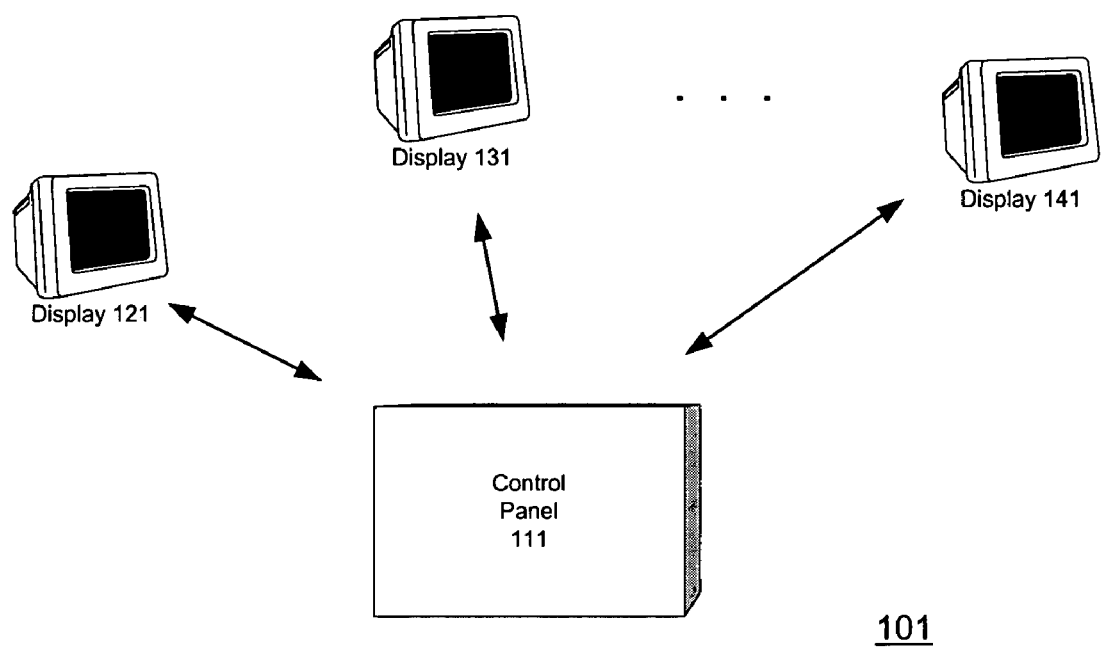
FIG. 1 is a block diagram illustrating one embodiment for the medical informatics system.

In one embodiment, a control monitor and user input device(s) are provided for use with the computer workstation to select medical images or series of medical images for viewing on the monitors. In general, the control monitor displays a plurality of images/series to allow the user of the computer workstation to select specific images for display on the monitors. FIG. 1 is a block diagram illustrating one embodiment for the medical informatics system. The medical informatics system 101 includes a control panel 111 with user input device(s) and a plurality of display monitor (e.g., 121, 131 and 141).

Figure 2:
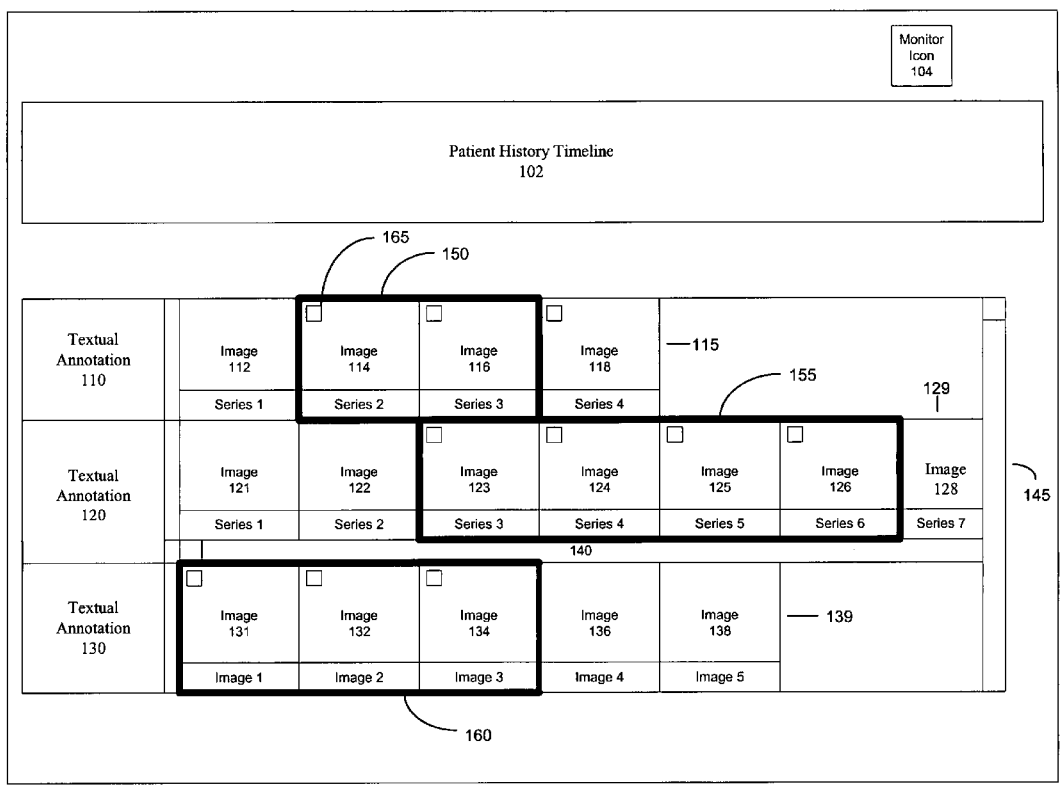
FIG. 2 illustrates an example control monitor display that shows a patient canvas view in accordance with one embodiment of the present invention.

In one embodiment, the control monitor displays a patient canvas view. In general, a patient canvas view permits a user to organize and navigate images/series for selected exams. FIG. 2 illustrates an example control monitor display that shows a patient canvas view in accordance with one embodiment of the present invention. A patient canvas view displayed on the control monitor includes a plurality of exams for the selected patient.

The area beneath the Patient History Timeline 102 is the primary display area for the selected exams and series/images. For the example of FIG. 2, three exams, arranged vertically on the screen, are shown. In one embodiment, selected exams (115, 129 and 139) are automatically laid out chronologically from top to bottom on the patient canvas view (i.e., the exams are laid out from the newest at the top to the oldest at the bottom). In another embodiment, the exams are laid out from left to right. Each exam is broken out left to right into one or more series for CT/MR and one or more images for CD/DR. In the example of FIG. 2, the first or top exam 115 includes the series of images labeled Series 1, Series 2, Series 3 and Series 4. The second exam 129, displayed on the second rack of the patient canvas view, currently displays seven series of images, labeled Series 1–7. The third exam 139, displayed on the third rack of the patient canvas view, currently displays five images.

In one embodiment, the patient canvas view is displayed in a standard orientation such that each horizontal scroll bar (e.g., scroll bar for the middle exam) contains an exam. The user, using the horizontal scroll bar, is permitted to scroll left and right to prompt the system to display the series/images contained within the exam. Also, a single vertical scroll bar (e.g., on the right of the control monitor) is provided to permit the user to scroll, in a vertical direction (i.e., from top to bottom), to display multiple exams.

The user may also use the features of the patient canvas view to organize images, within an exam, by re-arranging the relative horizontal positions among the images/series within an exam. In one embodiment, these organization operations are executed via a drag and drop operation. In a drag and drop operation, the user "selects" a series/image or exam with the cursor control device, and drags the series/image or exam to the destination location. When the image is located at the destination location, the user releases the series/image or exam to complete the drag and drop operation. When a user drags an image to a new location and drops the image over a second image, the system swaps the two images on the display. For example, if the system horizontally displays images 1, 2, 3, 4, 5 for an exam, and the user drops image #5 onto image #3, the system displays the images in the new order of 1, 2, 5, 4, 3.

A user may reposition thumbnail images within a navigation rectangle in order to reposition those images on the corresponding diagnostic monitor. For example, if the user moves the thumbnail located in the fourth position of a navigation rectangle to the second position, the fourth thumbnail image is swapped from pane four of the diagnostic monitor to pane two, and the second thumbnail image is swapped to the fourth pane four.

The patient canvas view on the user interface provides the functionality to "clone" an image. To this end, a user may copy an image or series, and paste the image or series in a different location. After a session, the selection and arrangement of exams and images/series are stored in a persistent datastore. When that user selects the same patient again, the patient canvas view is restored to the previous display from the prior session.

Diagnostic Monitor View for Navigation and Analysis of Images:

The medical informatics system permits a user to fully "navigate" the image. Typically, medical images are large, and cannot be displayed at full resolution on a computer monitor. Thus, when displayed in small windows, only portions of the medical image are displayed at any one time. The medical informatics system may display, in a 512×512 window, the entire source image at a lower resolution (i.e., a thumbnail sketch of the image).

The images displayed are "dynamic images." The images are dynamic because the user may fully manipulate each image to display different portions of the image (pan the original image) at different resolutions (zoom in and out). In one embodiment, a syntax provides full functionality to allow the user to manipulate the image in any manner desired. Starting with the lower resolution "dynamic image", the user may zoom-in on a more specific portion of the image. Thereafter, the user may pan the image to view a different portion of the image at the higher resolution. Accordingly, through the pan and zoom functions, the user may navigate through the images.

The medical informatics system permits a user to link series within the canvas. With this feature, as a user scrolls through slices of a first series, the second series, linked to the first series, is also scrolled. The medical informatics system also permits linking of any image or series, including images and series displayed in floating windows. The user interface also permits a user to clone a series for display at different window widths and window levels ("WW/WL") (i.e., contrast and brightness, respectively). The user interface further permits a user to scroll a CT/MR series to a particular slice, and then link this series to another series for simultaneous cine. In addition, the medical informatics system maintains, for simultaneous cine between two series, the same anatomical position for both series, even if the series contains a different number of slices or different slice spacings. For example, a first series may contain 100 slices within an anatomical position of a patient, and a second series may contain only 10 slices within the same anatomical position of the patient. For this example, the simultaneous cine feature displays 10 slices of the first series for every 1 slice of the second series. WW/WL acted upon any of the three display modes is inherited by subsequent display of that series or image during the current session. This includes larger windows created for a series or image. Multiple link channels are supported, as indicated by a number by a link icon and a drop down selection option at the point of linking. For this embodiment, the user may move through a single or link series with a scroll wheel on a cursor control device, pan and zoom around CR/DR images, and use the left button of the cursor control device to change WW/WL.

The medical informatics system synchronizes operations between the display images on the diagnostic monitors and the thumbnail images on the control monitor. For example, if user adjusts the WW/WL, the WW/WL adjustment is applied to both the display images on the diagnostic monitors and the thumbnail images on the control monitor.

Linked images and series may also be displayed in floating windows. In one embodiment for implementing this feature, the user double clicks on a linked image, or selects multiple series/images, to receive a display of a collage of those series/images, each displayed as a floating window. In this view, the user may cine through the series, as described above, linked or unlink two series, change the WW/WL with the right mouse button, or pan and zoom with a single or linked CT/DR images.

A double-click at the floating window level or zoom box control takes the user directly to the full screen display mode with the same image manipulation interactions. On a floating unlinked CT/MR series window, the user may use the scroll wheel to move the tile images back and forth one page at a time. A left-hand button on the cursor control device permits the user to WW/WL upon all the displayed images, so as to maintain persistence while scrolling the pages. In one embodiment for the nine-on-one tile mode, the size of each image within the window may comprise 256×256 pixels. In one embodiment, floating windows have basic intelligent layout properties, in that multiple floating windows stack using an offset of approximately 16 pixels to the right and 100 pixels down. As an additional feature, the floating windows have a button at the base of the window for prior image/series and next image/series control. Also, the floating windows have a link item menu available on the lower right corner of the image area, similar to the link button on the canvas. This allows shared pan zoom for plain images, shared cine for CT/MR series and shared page by page review for CT/MR series in tiled mode. Additionally, the user interface permits the user to toggle, using the cursor control device and keys, functionality between pan/zoom and slice navigation for CT/MR images.

The medical informatics system may display multiple images on the diagnostic monitors. In one embodiment, the medical informatics system displays images/series of images in different monitor configurations. The nomenclature used herein refers to monitor configurations in terms of "A×B", such that "A" defines the number of windows in the horizontal direction and "B" defines the number of windows in a vertical direction. For example, a monitor configuration of "2×3" displays two windows in the horizontal direction and three windows in the vertical direction, for a total of six windows.

The medical informatics system may also include a multi-image mode. For this embodiment, the system displays multiple images within a window. For example, a window may display a CT series. For this example, the user may desire to display, in the multi-image mode, four CT slices with the original window that displayed the CT series.

Navigation Rectangle:

The control monitor and input device (s) permit a user to set-up and change the layout of one or more diagnostic monitors using a navigation rectangle. The navigation rectangle allows the user to view images/series of an exam displayed on a diagnostic monitor. Through use of the navigation rectangle, the user selects an exam for display on a diagnostic monitor. The user is also permitted to quickly change the exam displayed on a diagnostic monitor. In addition to selecting and controlling the display of exams on diagnostic monitors, the navigation rectangle permits a user to select medical images/series associated with an exam. The navigation rectangle further allows the user to quickly change those images in an exam displayed on a diagnostic monitor.

Figure 3:
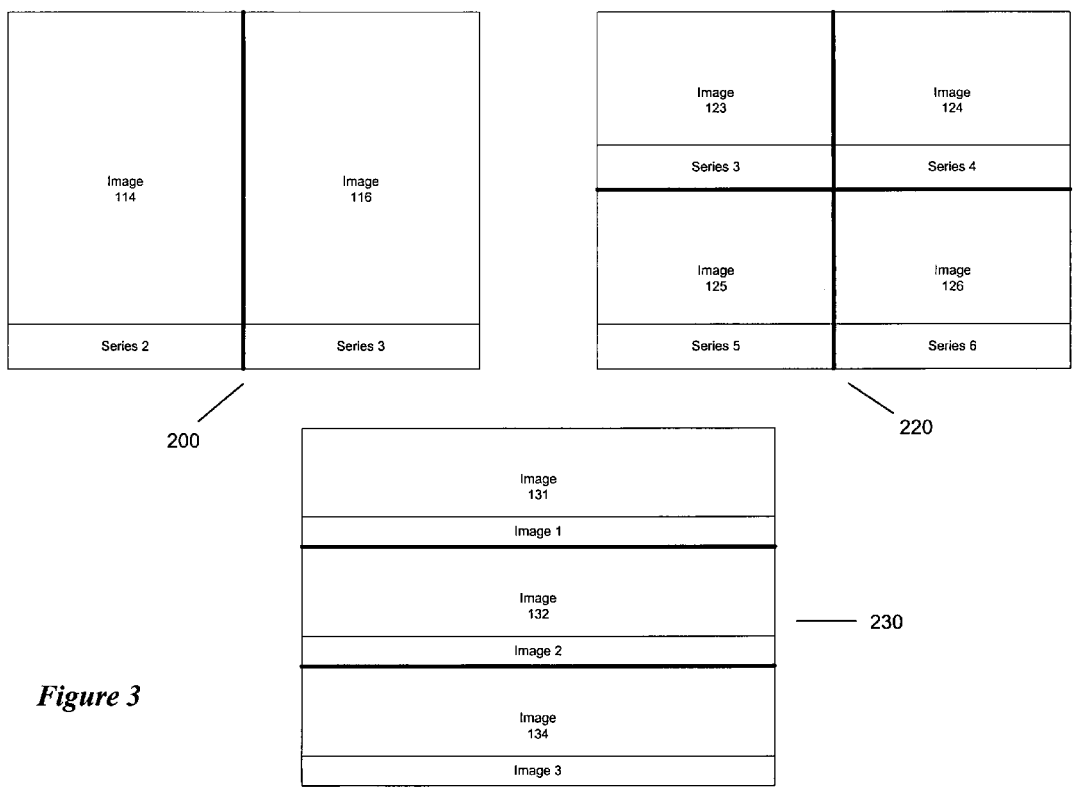
FIG. 3 illustrates example diagnostic monitors corresponding to the example navigation rectangles shown in FIG. 2.

In one embodiment, each navigation rectangle is associated with a single diagnostic monitor. FIG. 2 illustrates an example control panel incorporating the navigation rectangle of the present invention. FIG. 3 illustrates example diagnostic monitors corresponding to the example navigation rectangles shown in FIG. 2. For the example of FIGS. 2 and 3, navigation rectangle 150 (FIG. 2) is associated with diagnostic monitor 200 (FIG. 3), navigation rectangle 155 (FIG. 2) is associated with diagnostic monitor 220 (FIG. 3), and navigation rectangle 160 (FIG. 2) is associated with diagnostic monitor 230 (FIG. 3).

The diagnostic monitors shown in FIG. 2 include multiple panes. Diagnostic monitor 200 includes two panes (one for image 114 and one for image 116); diagnostic monitor 220 includes four panes (one for image 123, one for image 124, one for image 125, and one for image 126); and diagnostic monitor 230 includes three panes (one for image 131, one for image 132, and one for image 134).

Diagnostic monitor 200 (FIG. 2), configured in a 2×1 monitor mode, displays the second and third series (e.g., images 114 and 116) from exam 115 (i.e., the exam loaded on the top rack of the control monitor). As shown in FIG. 2, diagnostic monitor 220 is configured in a 2×2 monitor mode. Four (4) series, series 3–series 6, from exam 129 (FIG. 2) are displayed on diagnostic monitor 220. Diagnostic monitor 230 (FIG. 3), configured in a 1×3 monitor mode, displays the first three images (e.g., images 131, 132, and 134) from exam 139 (FIG. 2).

In one embodiment, the system displays images, encompassed by a navigation rectangle, on a diagnostic monitor from a left to right and top to bottom order. For example, image 123, the left most image in navigation rectangle 155 for exam 129 (FIG. 2), is displayed on diagnostic monitor 220 in the top right corner. The next image 124, located to the right of image 123, is displayed in the top right corner of diagnostic monitor 220. The third image from the left, image 125, is displayed in the lower left corner of diagnostic monitor 220. Finally, the fourth image, image 126, encompassed by navigation rectangle 155, is displayed in the lower right corner of diagnostic monitor 220.

In order to distinguish the different navigation rectangles associated with diagnostic monitors, each navigation rectangle is displayed with a unique color. In one embodiment, colors are associated with navigation rectangles as set forth in Table 1.

TABLE 1

| Diagnostic Monitor Number | Color |
| --- | --- |
| 1 | Red |
| 2 | Blue |
| 3 | Green |
| 4 | Yellow |

In one embodiment, a navigation rectangle only encapsulates images from a single exam. Thus, only images from a single exam are displayed on a diagnostic monitor. In another embodiment, a diagnostic monitor may be divided into multiple "panes" when the display monitor operates in a multi-image mode. In one embodiment, to divide the navigation rectangle, the user left click drags on a thumbnail icon of the image that the user desires to divide into a new navigation rectangle. In one embodiment, the medical informatics system permits the user to disable the function that splits the rectangle.

As shown in FIG. 2, the navigation rectangle is displayed on a rack for a corresponding exam. For example, navigation rectangle 155 is associated with exam 129 displayed on the middle rack, and navigation rectangle 160 is associated with exam 139 displayed on the bottom rack. The size of the navigation rectangle is set to encapsulate thumbnail images for those images displayed on the corresponding diagnostic monitor. For example, navigation rectangle 155 is sized to encapsulate four (4) series. The navigation rectangle resizes itself, as necessary, to contain the thumbnail images that are subsequently displayed on the diagnostic monitor panes.

If the diagnostic monitor configuration is such that there are more panes than thumbnail images, the navigation rectangle displayed on the control monitor encapsulates only those thumbnail images that are actually displayed on the diagnostic monitor. For example, a diagnostic monitor configuration may comprise a 4×1 configuration, and an exam may have three thumbnail images. For this example, the navigation rectangle is displayed on the control monitor to encapsulate only the three thumbnail images actually displayed on the diagnostic monitor (i.e., even though there is an empty pane in the diagnostic monitor).

The navigation rectangles are displayed on the control monitor to contain only as many thumbnail images as may be displayed on the current diagnostic monitor configuration. However, the navigation rectangle is displayed to encompass fewer thumbnail images if displaying all the thumbnail images result in an overlap to another navigation rectangle. For example, a first navigation rectangle may start at a first thumbnail image and may be associated with a first diagnostic monitor with a 4×1 configuration. For this example, a second navigation rectangle may start at a fourth thumbnail image, within the same exam associated with the first navigation rectangle, and may be associated with a diagnostic monitor that has a 1×1 monitor configuration. Although the first diagnostic monitor associated with the first navigation rectangle may display images 1–4, the first navigation rectangle only contains images 1–3 in order to avoid an overlap with the image contained within the second navigation rectangle. Thus, for this example, the last pane in the first diagnostic monitor is blank. However, if the user moves the second navigation rectangle to another thumbnail image (e.g., the fifth thumbnail image in the current exam), then the first navigation rectangle automatically places the fourth thumbnail image into the pane of the first diagnostic monitor because the overlap between the first and second navigation rectangles no longer occur.

In one embodiment, the order of thumbnail images displayed within the navigation rectangle follows the order of the panes for the corresponding diagnostic monitor from a left to a right direction. For this embodiment, the thumbnail image displayed in the left most position of the navigation rectangle is displayed in the first pane of the diagnostic monitor. Similarly, the thumbnail image displayed furthest to the right in the navigation rectangle is the image with the highest pane number on the diagnostic monitor. In another embodiment, the user may set the layout order to display the order of images from the control monitor on the panes on the diagnostic monitor in either a left to right or top to bottom order.

In one embodiment, the navigation rectangle is displayed with a thick grab bar on the left, top, and right side of the navigation rectangle. This readily permits a user to move the navigation rectangle to capture different images or a different exam. Also, the user may utilize the middle mouse button or wheel, with the cursor control device placed over the navigation rectangle, to move the navigation rectangle to capture different images or an exam. If the user left clicks and drags the grab bar, using the cursor control device, the system permits the user to move the navigation rectangle for placement on another exam or for placement over a different starting thumbnail image in the same exam. If the user drags a navigation rectangle, then the control monitor system auto scrolls the shelf and the racks, as necessary. The user may drag the navigation rectangle using the middle mouse button on a cursor control device as long as the drag operation does not start in the "zoom rectangle" of a thumbnail image.

The navigation rectangles may be associated with images originating from different types of modalities, including CT, MR, CR, etc. When the navigation rectangle is moved to another exam on a different modality, the diagnostic monitor configuration is changed based on the modality of the new exam. In one embodiment, the diagnostic monitor configuration is changed, when moving the navigation rectangle between exams with different modalities, as set forth below in Table 2.

TABLE 2

| Modality | Monitor Mode |
|---|---|
| CT | 1 × 1 (1 series) |
|  | 2 × 1 (2 or more series) |
| MR | 2 × 3 |
| CR | 1 × 1 |
| Others | 1 × 1 (1 series) |
|  | 2 × 1 (2 or more series) |

The navigation rectangles do not overlap thumbnail images. For example, if a thumbnail image is contained within a first navigation rectangle, that thumbnail image is not contained within another navigation rectangle. As a result, the same thumbnail image is not displayed on more than one diagnostic monitor at a single time. The system enforces this rule such that the user may not position two navigation rectangles to encapsulate the same image. If the user attempts to place a first navigation rectangle over images of a second navigation rectangle, then the first navigation rectangle is resized to encompass the images, and the second navigation rectangle is contracted to the remaining images. For example, if the second navigation rectangle encompasses images horizontally arranged as images 1, 2, 3 and 4, and the first navigation rectangle is dropped on image #3, then the second navigation rectangle is resized to cover images #1 and #2, and the first navigation rectangle is resized to cover images #3 and #4.

The control system also permits a user to change the thumbnail images of an exam displayed on a corresponding diagnostic monitor. For example, a navigation rectangle may encompass the first four of seven thumbnail images for an exam displayed on a shelf of a control monitor. For this example, the diagnostic monitor may display the images in a 4×1 monitor configuration. If the user shuffles the fifth thumbnail image to replace the fourth thumbnail image in the navigation rectangle, the system swaps the fourth image with the fifth image in the fourth pane of the diagnostic monitor.

The system also permits the user to change the monitor configuration of a navigation rectangle. However, if the user changes the monitor configuration of a navigation rectangle that results in an overlap with another navigation rectangle, then the change is effectuated, but the navigation rectangles are displayed such that they do not overlap. This operation may cause blank (e.g., black) areas on the diagnostic monitors. For example, under this scenario, the navigation rectangle that was dragged onto the other navigation rectangle causes the system to align the first navigation rectangle next to the second navigation rectangle and encompass those images that are available. If fewer images are loaded into the rack of the control monitor than the number of monitors, the navigation rectangle is hidden. If a navigation rectangle is hidden, it is displayed as soon as an additional image is loaded onto the rack. For example, a new image may be loaded onto the rack by loading a new exam or by cloning an existing exam.

The navigation rectangle may be used with a diagnostic monitor divided into more than one diagnostic monitor. A feature allows the user to "push" navigation rectangles displayed on the control monitor. When dragging the left-hand monitor navigation rectangle to the right side, the system presents the image that the navigation rectangle is dragged over. If the left-hand monitor navigation rectangle meets the right-hand monitor navigation rectangle and the user presses a key (e.g., F7), the left-hand monitor navigation rectangle pushes the right-hand monitor navigation rectangle to the right. This results in the image presented in the right-hand monitor to shift to the left-hand monitor, and the new image is presented in the right-hand monitor. When dragging the right hand monitor navigation rectangle to the left side, the system presents the image that the navigation rectangle is dragged over. When the right-hand monitor reticule meets the left-hand monitor navigation rectangle and the user presses a key (e.g., F8), the right hand monitor navigation rectangle pushes the left-hand monitor navigation rectangle towards the left side. This results in shifting the image presented in the left-hand monitor to the right-hand monitor, and a new image is presented in the left-hand monitor.

As used herein, "current monitor", when used in conjunction with a description of a user interface operation, refers to the monitor that corresponds to a navigation rectangle identified by the user's cursor control device. For example, if the user places a cursor over a navigation rectangle, then the "current monitor" is the monitor that corresponds to that navigation rectangle.

In one embodiment, the informatics system provides an option to "Bind to Monitor X", wherein X identifies the monitor to the left of the current monitor. For this embodiment, the "Bind to Monitor X" function is presented to the user from a right click menu. When the user invokes the "Bind to Monitor X" function, the system binds the two navigation rectangles together such that operations performed on the bound navigation rectangles are applied across both diagnostic monitors. In one embodiment, the system indicates that the diagnostic monitors are bound by displaying an icon on the control monitor for the bound navigation rectangles. An "Unbind Monitors" function permits the user to "unbind" monitors, if previously bound. In one embodiment, the "Unbind Monitors" function is presented to the user from a right click menu.

In one embodiment, the informatics system displays pane icons within images/series encompassed by a navigation rectangle. As shown in FIG. 2, each series/image encompassed by a navigation rectangle includes a pane icon (i.e., unless the monitor is configured in a 1×1 mode). In FIG. 2, the pane icon for image 114 is labeled 165. For this embodiment, the pane icon is displayed in the upper left hand corner of the image. In one embodiment, the pane icon is displayed with the same color as the navigation rectangle (i.e., the color of the navigation rectangle corresponds to a diagnostic monitor). In general, the pane icon indicates the position of the image displayed on the diagnostic monitor.

Figure 4:
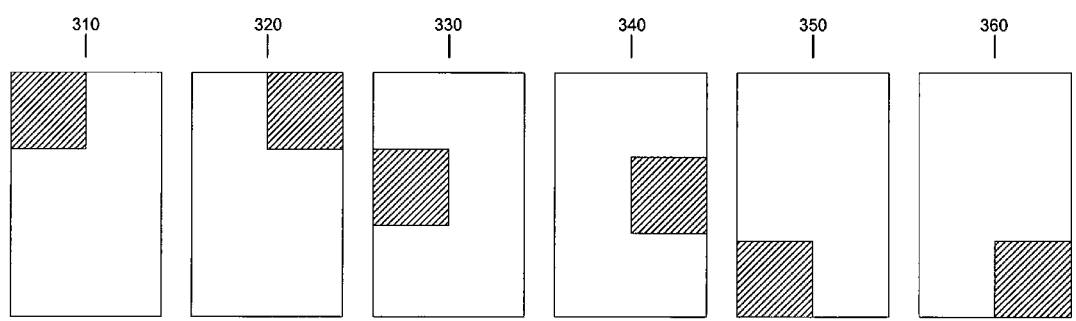
FIG. 4 illustrates one embodiment for displaying location of an image using the pane icon.

FIG. 4 illustrates one embodiment for displaying location of an image using the pane icon. The pane icon specifies, for each image displayed on a diagnostic monitor, a location of the image on the diagnostic monitor. For this example, the diagnostic monitor is configured in a 2×3 mode. The pane icon 310, when displayed on an image, indicates that the image is displayed in the upper left corner pane of the corresponding diagnostic monitor. A pane icon 320 indicates that the corresponding image is displayed in the upper right corner pane of the diagnostic monitor. Similarly, pane icons 330, 340, 350 and 360 show relative locations of panes that display the images on the diagnostic monitor. In one embodiment, the thumbnail images are displayed from left to right on a rack of the control panel. The images, corresponding to the thumbnail images, are displayed on the panes of the diagnostic monitor starting from left to right and then top to bottom. For the example shown in FIG. 4, the pane icons are displayed in images on the control panel in the order shown in FIG. 4 (e.g., pane icon 310 appears in the left most image in the navigation rectangle, and pane icon 360 appears in the right most image in the navigation rectangle).

In one embodiment, the system permits navigation rectangle to operate in "segments." A navigation rectangle segment manages one or more contiguous panes in a diagnostic monitor. For example, if the diagnostic monitor is configured in a M6P mode, a navigation rectangle segment may manage between one and six of these panes. A single pane on a diagnostic monitor is not managed by more than one navigational rectangle segment unless the corresponding diagnostic monitors are bound.

A navigation rectangle segment is associated with a single diagnostic monitor (i.e., a navigation rectangle segment does not manage panes from more than one diagnostic monitor). A user may move a navigation rectangle segment by left click dragging the navigation rectangle border. To move a navigation rectangle segment, the user conducts a middle button dragging operation from a covered thumbnail window. A navigation rectangles segment may be split into two segments by left click dragging from the pane icon in the thumbnail window.

In one embodiment, if the user right clicks on the border of a navigation rectangle segment, a menu is displayed. The menu provides a means for the user to invoke the functions "Hide", "New segment", "Combine Segment", "Bind Rectangles", and "Unbind Rectangles." The Hide function, when invoked, removes the navigation rectangle segment from a control monitor rack. If the user desires to return the navigation rectangle segment to the rack, the user conducts a left click dragging operation using the monitor icon. The "New Segment" function, when selected, splits that navigation rectangle segment into two navigation rectangle segments. The new segment starts at the thumbnail identified by the user's cursor control device. The New Segment operation is only effectuated if the thumbnail, identified during the right click operation, is not the first thumbnail in the segment.

The "Combine Segment" function, when selected by the user, combines the current segment with the segment that covers the thumbnail preceding the starting thumbnail for the current segment. The combine segment function is not invoked if the segment covers the first pane of a monitor.

The "Bind Rectangle" function, when selected, binds the current segment with the segment that covers the thumbnail preceding the starting thumbnail for the current segment. The Bind Rectangle function allows two segments from different diagnostic monitors to function as a single navigation rectangle. The Bind Rectangles function only takes effect if there is a segment immediately to the right of the first thumbnail of the current segment. The "Unbind Rectangle" function, when selected by a user, separates two previously bound navigation rectangle segments from different monitors. The "Unbind Rectangle" function separates a current segment from a segment that covers the thumbnail preceding the starting thumbnail for the current second.

To create a navigation rectangle segment, the user left click drags the monitor icon at the top of the control monitor screen (e.g., monitor icon 104, FIG. 2) to create a single navigation rectangle segment. The user may then drop the navigation rectangle segment so as to cover all panes for that diagnostic monitor. In one embodiment, if the user creates a single navigation rectangle segment, all navigation rectangle segments previously associated with this diagnostic monitor are destroyed. This feature allows the user to quickly recombine all navigation rectangle segments into a single navigation rectangle segment. If a navigation rectangle segment is removed, it is no longer visibly displayed in a rack on the control monitor. The user may reload that monitor using the monitor icon (e.g., monitor icon 104, FIG. 2).

In one embodiment, the user may set the monitor mode for a diagnostic monitor. In one implementation for this feature, the user selects a monitor mode from a pull down menu. The pull down menu is displayed when the user right clicks the cursor control device when the cursor is located over the monitor icon or the pane icon.

If the user changes the monitor mode and the new monitor mode displays fewer panes, then the segments that encompassed the deleted panes are shortened or destroyed if no panes remain for that segment. Also, if the user changes the monitor mode such that more panes are displayed in the new monitor mode, then the segment, which covered the last pane in the previous mode, is extended to cover the newly created panes. If a user places a navigation rectangle segment over a first thumbnail managed by another segment, then those two segments swap positions.

A segment is displayed only for those thumbnail images currently covered by that segment. A first segment does not overlap with another segment. In one embodiment, the segment does not display any indicator for empty panes. This behavior is necessary to handle the following situations. In the first situation, there may be fewer thumbnail windows than panes in a diagnostic monitor. If the monitor is configured in a 2×3 mode and there is a single segment for that monitor placed on an exam with only four windows, then there are two empty panes and only four images for display. The segment is only created for those visible thumbnails, such that the segment shall not be displayed for the two empty panes. In a second situation, a first segment may cover six panes, and a second segment may overlap the first segment. For this example, a monitor may be configured in a M6P mode with a single segment and a second diagnostic monitor may be configured in a M6P mode with a single segment. Under this scenario, a single exam with six thumbnails is loaded, and the first navigation rectangle starts on pane one. The segment for the second diagnostic monitor starts on pane number four. Although the first navigation rectangle may display six panes, the second navigation rectangle is managing thumbnail windows 4 to 6. Under this scenario, the last three panes on both the diagnostic monitors are empty.

In one embodiment, the informatics system implements hanging protocols. In general, hanging protocols provide a means for the system to save the state of displaying exams. For example, a user may display, in a first session, one or more exams on diagnostic monitors using the system. During the first session, the user may arrange the display of the exams on the diagnostic monitors. When the user exits, the system saves the state of the first session, such that the display location of the exams on the diagnostic monitors is saved. When the user views the exams in a subsequent second session, the exams are displayed on the diagnostic monitor in the same presentation as the first session. In addition, if the user specifies segments during the first session, the segments are also presented in the second session. In one embodiment, if an exam has not been previously displayed, the system presents the exam (i.e., default hanging protocol) based on 1) the modality type that acquired the exam; and then 2) the body part that is the subject of the exam.

In one embodiment, the system uses an exam code grouping to reference a single hanging protocol for multiple exams. For this embodiment, one or more exams are organized into an exam grouping, and the system assigns a unique identifier to the exam grouping. This technique minimizes storage resources on the computer by only storing hanging protocols (state information) for exam code grouping.

Figure 5:
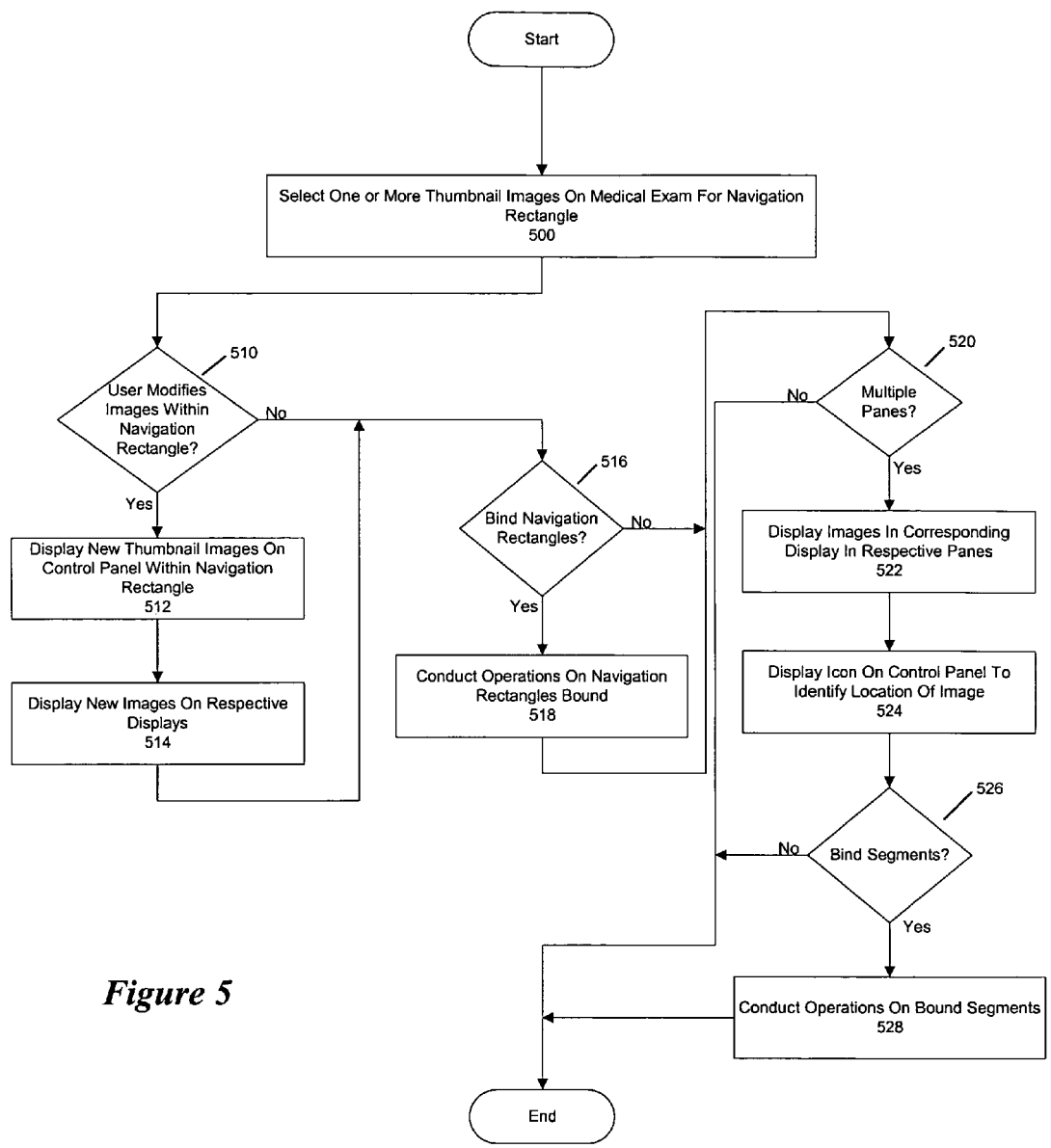
FIG. 5 is a flow diagram illustrating one embodiment for the operational flow of the software in the medical informatics system.

FIG. 5 is a flow diagram illustrating one embodiment for the operational flow of the software in the medical informatics system. The navigation rectangle(s) are selected for one or more thumbnail images of a medical exam (block 500, FIG. 5). A user may modify the thumbnail images encompassed by the navigation rectangle. For example, the user may change the thumbnail images within an exam, select more or less thumbnail images for the navigation rectangle, or move the navigation rectangle to another exam. If the user modifies the thumbnail images within a navigation rectangle, then the system displays the navigation rectangle that encompasses the new set of thumbnail images (blocks 510 and 512, FIG. 5). Also, the new images, encompassed by the navigation rectangle, are displayed on the display monitors (blocks 514, FIG. 5).

If the user selects the function to bind navigation rectangles, then subsequent operations on the bound navigation rectangles are performed as a single navigation rectangle (blocks 516 and 518, FIG. 5). If the user displays the images on the display monitor in multiple panes, then the images are displayed as indicated by the display icons on the control panel (blocks 520, 522 and 524, FIG. 5). If the user selects the function to bind segments of the panes, then subsequent operations on the bound segments are performed as a single pane (blocks 526 and 528, FIG. 5).

Although the present invention has been described in terms of specific exemplary embodiments, it will be appreciated that various modifications and alterations might be made by those skilled in the art without departing from the spirit and scope of the invention.

The invention claimed is:

1. A method for controlling display of medical images, said method comprising the steps of:
    displaying a plurality of thumbnail size medical images on a control panel;
    displaying, on said control panel, a first navigation rectangle that encompasses a first set of thumbnail size medical images comprising at least one of said thumbnail size medical images displayed on said control monitor;
    displaying, on a first display, at least one medical image that corresponds to said first set of thumbnail size medical images;
    displaying, on said control panel, a second navigation rectangle that encompasses a second set of thumbnail size medical images comprising at least one of said thumbnail size medical images displayed on said control monitor; and
    displaying, on a second display, at least one medical image that corresponds to said second set of thumbnail size medical images.

2. The method as set forth in claim 1, further comprising the steps of:
    displaying images for at least one medical exam on said control panel, said images for said medical exam comprising a plurality of said thumbnail size medical images;
    receiving user input to select at least one thumbnail size medical image of a medical exam for a navigation rectangle;

displaying, on said control panel, in response to said user input, a navigation rectangle that encompasses said thumbnail size medical image for said medical exam selected; and displaying, on a display, at least one medical image that corresponds to said thumbnail size medical image.

3. The method as set forth in claim 2, further comprising the steps of:

receiving user input to replace at least one thumbnail size medical image of a medical exam with at least one different thumbnail size medical image of said medical exam;

displaying, on said control panel, in response to said user input, a new navigation rectangle that encompasses said different thumbnail size medical image selected; and displaying, on a display, at least one medical image that corresponds to said different thumbnail size medical image.

4. The method as set forth in claim 1, further comprising the steps of:

receiving user input to select at least one additional thumbnail size medical image;

displaying, on said control panel, in response to said user input, a new navigation rectangle that encompasses said additional thumbnail size medical image selected; and displaying, on a display, at least one medical image that corresponds to said additional thumbnail size medical image.

5. The method as set forth in claim 1, wherein the step of displaying, on a first display, at least one medical image that corresponds to said first set of thumbnail size medical images comprises the step of displaying a plurality of medical images, each in a window pane on said first display.

6. The method as set forth in claim 5, further comprising the step of displaying, in a portion of a thumbnail image on said control panel, a pane icon that identifies a location of a pane for said corresponding medical image displayed on said display.

7. The method as set forth in claim 1, further comprising the steps of:

receiving user input to reposition at least one thumbnail size medical image within said navigation rectangle;

displaying, on said control panel, in response to said user input, said navigation rectangle that encompasses said repositioned thumbnail size medical image; and displaying, on a display, said medical images in an order that corresponds to said repositioned thumbnail size medical images.

8. The method as set forth in claim 1, further comprising the steps of:

generating a plurality of virtual monitors for a single display;

displaying, on said control panel, a first navigation rectangle that encompasses a first set of thumbnail size medical images comprising at least one of said thumbnail size medical images displayed on said control monitor;

displaying, within a first virtual monitor on said display, at least one medical image that corresponds to said first set of thumbnail size medical images;

displaying, on said control panel, a second navigation rectangle that encompasses a second set of thumbnail size medical images comprising at least one of said thumbnail size medical images displayed on said control monitor; and displaying, within a second virtual monitor on said display, at least one medical image that corresponds to said second set of thumbnail size medical images.

9. The method as set forth in claim 1, further comprising the steps of:

receiving user input to bind at least two navigation rectangles;

receiving user input to conduct an operation on said two navigation rectangles;

conducting, in response to said input, said operation on both of said navigation rectangles displayed on said control panel; and conducting said operation so as to effectuate two monitors that correspond to said two navigation rectangles bound.

10. The method as set forth in claim 1, further comprising the steps of:

displaying a plurality of window panes on a display, such that said window panes divide said display into a plurality of sections;

displaying a plurality of medical images, each in a window pane of said display;

receiving user input to generate a segment for at least two window panes;

receiving user input to conduct an operation on said segment;

conducting, in response to said input, said operation on said segment displayed on said control panel; and conducting said operation so as to effectuate said two window panes that correspond to said segment.

11. A medical informatics system comprising:

control panel for displaying a plurality of thumbnail size medical images, for displaying a first navigation rectangle that encompasses a first set of thumbnail size medical images comprising at least one of said thumbnail size medical images displayed on said control monitor, and for displaying a second navigation rectangle that encompasses a second set of thumbnail size medical images comprising at least one of said thumbnail size medical images displayed on said control monitor;

first display, coupled to said control panel, for displaying at least one medical image that corresponds to said first set of thumbnail size medical images; and second display for displaying at least one medical image that corresponds to said second set of thumbnail size medical images.

12. The medical informatics system as set forth in claim 11, further comprising input device, coupled to said control panel, for receiving user input to select at least one thumbnail size medical image of a medical exam for a navigation rectangle; and wherein:

said control panel further for displaying images for at least one medical exam, said images for said medical exam comprising a plurality of said thumbnail size medical images;

said control panel for displaying in response to said user input, a navigation rectangle that encompasses said thumbnail size medical image for said medical exam selected; and said display for displaying at least one medical image that corresponds to said thumbnail size medical image.

13. The medical informatics system as set forth in claim 12, further comprising an input device for receiving user input to replace at least one thumbnail size medical image of a medical exam with at least one different thumbnail size medical image of said medical exam, and wherein:

said control panel for displaying, in response to said user input, a new navigation rectangle that encompasses said different thumbnail size medical image selected; and said display for displaying, on a display, at least one medical image that corresponds to said different thumbnail size medical image.

14. The medical informatics system as set forth in claim 10, further comprising an input device for receiving user input to select at least one additional thumbnail size medical image, and wherein:

said control panel for displaying, in response to said user input, a new navigation rectangle that encompasses said additional thumbnail size medical image selected; and said display for displaying at least one medical image that corresponds to said additional thumbnail size medical image.

15. The medical informatics system as set forth in claim 10, wherein said display for displaying a plurality of medical images, each in a window pane on said display.

16. The medical informatics system as set forth in claim 15, wherein said control panel for displaying, in a portion of a thumbnail image, a pane icon that identifies a location of a pane for said corresponding medical image displayed on said display.

17. The medical informatics system as set forth in claim 10, further comprising an input device for receiving user input to reposition at least one thumbnail size medical image within said navigation rectangle; and wherein:

said control panel for displaying, in response to said user input, said navigation rectangle that encompasses said repositioned thumbnail size medical image; and said display for displaying said medical images in an order that corresponds to said repositioned thumbnail size medical images.

18. The medical informatics system as set forth in claim 10, wherein:

said display further comprising a plurality of virtual monitors;

said control panel for displaying a first navigation rectangle that encompasses a first set of thumbnail size medical images comprising at least one of said thumbnail size medical images displayed on said control panel;

said first virtual monitor for displaying at least one medical image that corresponds to said first set of thumbnail size medical images;

said control panel for displaying a second navigation rectangle that encompasses a second set of thumbnail size medical images comprising at least one of said thumbnail size medical images displayed on said control panel; and said second virtual monitor for displaying at least one medical image that corresponds to said second set of thumbnail size medical images.

19. The medical informatics system as set forth in claim 10, further comprising:

input device for receiving user input to bind at least two navigation rectangles and for receiving user input to conduct an operation on said two navigation rectangles; and software for conducting, in response to said input, said operation on both of said navigation rectangles displayed on said control panel, and for conducting said operation so as to effectuate two monitors that correspond to said two navigation rectangles bound.

20. The medical informatics system as set forth in claim 10, further comprising:

a plurality of window panes displayed on said display, such that said window panes divide said display into a plurality of sections, each window pane for displaying a medical image;

input device for receiving user input to generate a segment for at least two window panes and for receiving user input to conduct an operation on said segment;

software for conducting, in response to said input, said operation on said segment displayed on said control panel, and for conducting said operation so as to effectuate said two window panes that correspond to said segment.

21. A computer readable medium comprising a plurality of instructions, which when executed, causes the computer to perform the steps of:

displaying a plurality of thumbnail size medical images on a control panel;

displaying, on said control panel, a first navigation rectangle that encompasses a first set of thumbnail size medical images comprising at least one of said thumbnail size medical images displayed on said control monitor;

displaying, on a first display, at least one medical image that corresponds to said first set of thumbnail size medical images;

displaying, on said control panel, a second navigation rectangle that encompasses a second set of thumbnail size medical images comprising at least one of said thumbnail size medical images displayed on said control monitor; and displaying, on a second display, at least one medical image that corresponds to said second set of thumbnail size medical images.

22. The computer readable medium as set forth in claim 21, further comprising the steps of:

displaying images for at least one medical exam on said control panel, said images for said medical exam comprising a plurality of said thumbnail size medical images;

receiving user input to select at least one thumbnail size medical image of a medical exam for a navigation rectangle;

displaying, on said control panel, in response to said user input, a navigation rectangle that encompasses said thumbnail size medical image for said medical exam selected; and displaying, on a display, at least one medical image that corresponds to said thumbnail size medical image.

23. The computer readable medium as set forth in claim 22, further comprising the steps of:

receiving user input to replace at least one thumbnail size medical image of a medical exam with at least one different thumbnail size medical image of said medical exam;

displaying, on said control panel, in response to said user input, a new navigation rectangle that encompasses said different thumbnail size medical image selected; and displaying, on a display, at least one medical image that corresponds to said different thumbnail size medical image.

24. The computer readable medium as set forth in claim 21, further comprising the steps of:

receiving user input to select at least one additional thumbnail size medical image;

displaying, on said control panel, in response to said user input, a new navigation rectangle that encompasses said additional thumbnail size medical image selected; and displaying, on a display, at least one medical image that corresponds to said additional thumbnail size medical image.

25. The computer readable medium as set forth in claim 21, wherein the step of displaying, on a first display, at least one medical image that corresponds to said first set of thumbnail size medical images comprises the step of displaying a plurality of medical images, each in a window pane on said first display.

26. The computer readable medium as set forth in claim 25, further comprising the step of displaying, in a portion of a thumbnail image on said control panel, a pane icon that identifies a location of a pane for said corresponding medical image displayed on said display.

27. The computer readable medium as set forth in claim 21, further comprising the steps of:

receiving user input to reposition at least one thumbnail size medical image within said navigation rectangle;

displaying, on said control panel, in response to said user input, said navigation rectangle that encompasses said repositioned thumbnail size medical image; and displaying, on a display, said medical images in an order that corresponds to said repositioned thumbnail size medical images.

28. The computer readable medium as set forth in claim 21, further comprising the steps of:

generating a plurality of virtual monitors for a single display;

displaying, on said control panel, a first navigation rectangle that encompasses a first set of thumbnail size medical images comprising at least one of said thumbnail size medical images displayed on said control monitor;

displaying, within a first virtual monitor on said display, at least one medical image that corresponds to said first set of thumbnail size medical images;

displaying, on said control panel, a second navigation rectangle that encompasses a second set of thumbnail size medical images comprising at least one of said thumbnail size medical images displayed on said control monitor; and displaying, within a second virtual monitor on said display, at least one medical image that corresponds to said second set of thumbnail size medical images.

29. The computer readable medium as set forth in claim 21, further comprising the steps of:

receiving user input to bind at least two navigation rectangles;

receiving user input to conduct an operation on said two navigation rectangles;

conducting, in response to said input, said operation on both of said navigation rectangles displayed on said control panel; and conducting said operation so as to effectuate two monitors that correspond to said two navigation rectangles bound.

30. The computer readable medium as set forth in claim 21, further comprising the steps of:

displaying a plurality of window panes on a display, such that said window panes divide said display into a plurality of sections;

displaying a plurality of medical images, each in a window pane of said display;

receiving user input to generate a segment for at least two window panes;

receiving user input to conduct an operation on said segment;

conducting, in response to said input, said operation on said segment displayed on said control panel; and conducting said operation so as to effectuate said two window panes that correspond to said segment.

* * * * *